Figure 1:
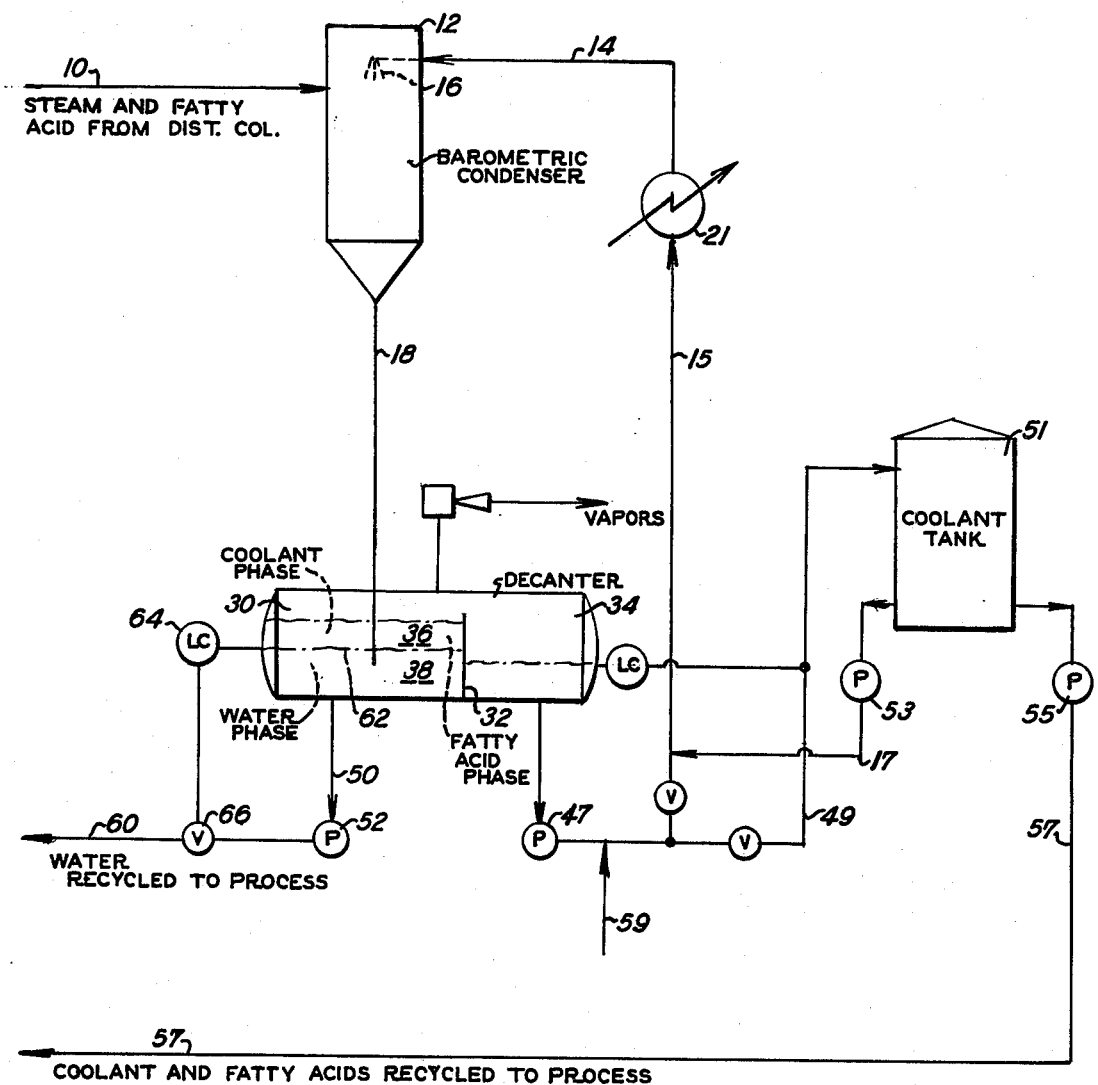

United States Patent [19]

Graham et al.

[11] 4,188,290
[45] Feb. 12, 1980

[54] POLLUTION CONTROL FOR FATTY ACID CONDENSATION

[75] Inventors: James J. Graham, Wayland, Mass.; Roger J. Vernon, Maidenhead, England

[73] Assignee: The Badger Company, Cambridge, Mass.

[21] Appl. No.: 811,329

[22] Filed: Jun. 29, 1977

[51] Int. Cl.² .......................... B01D 5/00; B01D 21/00
[52] U.S. Cl. ........................................ 210/21; 210/60; 210/71; 210/83; 260/424; 260/428.5; 55/85; 55/89; 203/42; 203/87
[58] Field of Search ...................... 210/21, 60, 69, 70, 210/71, 83; 55/80, 85, 89; 261/7; 260/412.2, 419, 428, 424, 428.5; 202/182, 183, 184, 185 R, 199, 202, 205; 203/39, 42, 87, 91, 92, 93, 94, 95, 96, 97

[56] References Cited

U.S. PATENT DOCUMENTS

| | | | |
|---|---|---|---|
| 2,747,680 | 5/1956 | Kilpatrick | 55/85 |
| 3,061,622 | 10/1962 | Fiala | 260/428 |
| 3,622,466 | 11/1971 | West | 203/1 |
| 3,634,201 | 1/1972 | Kehse | 203/42 |
| 3,709,793 | 1/1973 | Bress | 202/182 |
| 4,065,273 | 12/1977 | Rudolph | 55/50 |

OTHER PUBLICATIONS

Bailey's Industrial Oil and Fat Products, 3rd ed., 1964, Interscience Publishers, New York, pp. 64, 59, 58, 176, 226.

Primary Examiner—Charles N. Hart
Assistant Examiner—David R. Sadowski

[57] ABSTRACT

Steam carrying fatty acids is contacted in a barometric condenser with a cooling medium comprising a fatty acid having between six and eighteen carbon atoms to produce a liquid organic phase containing the fatty acids which were entrained in the steam, and an aqueous phase, such phases being readily separated by decantation. After separation of the phases, a portion of the organic phase is used for the cooling medium.

6 Claims, 2 Drawing Figures

SOLIDIFICATION POINTS
OCTANOIC = PALMITIC
FATTY ACID MIXTURES

POLLUTION CONTROL FOR FATTY ACID CONDENSATION

The invention relates to a non-polluting system including separation of fatty acids from steam in an oil or fatty acid purification system using a cooling medium comprising a fatty acid having from about six to eighteen carbon atoms, with recycle of separated cooling medium and water and recovery of the fatty acids to avoid discharge of the fatty acid contaminated water to waste.

In the treatment of fixed oils, and sometimes fatty acids with steam to remove certain or all of the fatty acids from the parent fixed oil, in its purification by steam vaporization, the steam carrying the fatty acid, partially as vapors and partially as entrained liquids, is usually passed to a barometric condenser for cooling contact with water or other liquid condensing medium, whereby both steam and the entrained fatty acids are usually condensed under conditions of reduced pressure. In that general cooling process, the fatty acids both condense and freeze out as suspended solids and/or as dispersed and emulsified liquids in the condensate. Under these conditions, the fatty acids usually tend to accumulate in the cooling tower basin and create a waste disposal problem. The fatty acids condensed and deposited in various conditions between liquids and solids and in various states of suspension and emulsification, variable with the specific freezing points of individual fatty acid components, are usually present as a sludge difficult to separate into its water and organic components. Even efforts to dispose of water with only small residual quantities of fatty acids to the sewers has presented a pollution and sewage disposal problem since the presence of the fatty acid greatly increases the oxygen demand of such waters, rendering the presence of any fatty acids undesirable and difficult to handle in normal sewage disposal.

It was also proposed in the art to maintain fatty acid-steam vapors at a high enough temperature to scrub out entrained fatty acid liquids using liquid condensed fatty acids as scrubbing liquid, but the steam vapors still contain light fatty acids to pollute the steam condensate and the heavy fatty acids solidify in the solvent wash oil.

According to this invention, the cooling liquid passed to the barometric condenser comprises a fatty acid which is miscible with the fatty acids suspended in the steam. The fatty acid contaminated steam is condensed by cooling contact such as spraying with this cooled organic liquid, and the fatty acids therein dissolve in the cooling liquid. The condensate is separated into phases. The heavier fatty acids in the organic phase are controlled in quantity to less than about 30%. The separated organic phase, after temperature and quantity readjustment, is recycled to the barometric condenser. The separated water is returned to the process, such as for reconversion to process steam or reuse as process water.

The coolant comprises a fatty acid having from about 6 to 18 carbon atoms. Preferably the acids in the range of 15 to 18 carbon atoms are unsaturated. Typical higher unsaturated fatty acids are oleic and linoleic. Typical lower saturated fatty acids are octanoic, decanoic and lauric.

The cooling liquid is adjusted in quantity and temperature as needed to condense all of the steam as well as the fatty acids entrained therein. Higher fatty acids entrained in the steam, typically acids having from 14 to 20 carbon atoms, such as stearic or palmitic acids, tend to solidify as they are cooled and at lower temperatures as the content of such acids in the cooling medium progressively increase.

The temperature of the cooling medium including the condensate is maintained high enough to prevent crystallization of the higher fatty acids after they begin to accumulate in substantial quantity. Hence, the temperature of condensation and decantation will generally be maintained as high as practical, that is, below the condensation temperature of the water, usually under vacuum such as below about 175° F. and down to an intermediate raised temperature of about 80° F. The upper temperature limit is dictated by the economy and thermodynamics of heating the cooling fluid as high as practical to effect the condensation of the steam and fatty acids and to prevent substantial accumulations of the higher fatty acids from separating out. The lower temperature limit may be about 80° F., which is an intermediate temperature raised only enough to prevent crystallization and separation of the higher acids in some practical quantity above about 10% by weight, with a preferred range of 15 to 40% weight, whereby the separated fatty acids will remain effectively fluid and of low enough viscosity for handling. Again, the temperature of the condensate is preferably adjusted to the range of about 140° F. to 165° F. to allow formation of a distinct interface between the aqueous and oily layers of condensate, whereby the condensed water is easily separated from the fatty acid layer for reuse in the process.

Referring to the drawing FIG. 1, steam contaminated with entrained liquid and vapors of fatty acid, typically resulting from purification of soy bean oil by aerating with steam, and containing a small quantity of higher fatty acids, typically about 0.8 to 1.2% of the vaporous mixture, is passed through line 10 to a barometric condenser 12. It is washed and cooled with a spray of a cooling liquid containing a 6 to 18C=atom fatty acid such as fleic or octanoic acid from line 14 and nozzle 16, in quantity sufficient to cool and condense all of the steam and fatty acids. The coolant fatty acid in contact with the steam is at a temperature in the range of 80° to 175° F., usually between about 140° and 165° F., to produce a warm condensate in which the condensed fatty acid not only will not freeze out but preferably will form an easily separable organic liquid phase.

As shown in FIG. 1, the steam contaminated with fatty acids in line 10 enters the barometric condenser 12 and is washed, cooled and condensed by a spray of coolant comprising a fatty acid such as oleic acid or octanoic acid from a nozzle 16 passed thereto by a duct 14 as recycled coolant from a decantation tank 30. The washed and condensed steam is withdrawn from the bottom of the condenser 12 by way of line 18, passing thence to the decantation tank 30. The accumulated liquids in tank 30 separate into distinct layers 36 and 38 at an interface level 62 controlled by liquid level controller 64 operating a valve 66. The lower aqueous layer is withdrawn by pump 52 by way of line 50 at a rate controlled by valve 66 and the water is returned by way of line 60 to the plant for reuse.

The organic or solvent fatty acid phase 36 overflows the partition 32 and is passed by way of pump 47 and line 49 to a coolant tank 51. A portion of the organic phase is withdrawn by pump 53 and returned to line 15 as recycled coolant by way of line 17. The temperature of the coolant is adjusted in a surface type heat exchanger 21 to control the temperature of the organic fatty acid coolant in the selection range of 80° to 175° F., usually above 85° F. A second pump 55 withdraws fatty acid solution from the bottom of the coolant tank 51 and returns the same to the plant for further processing to separate the higher fatty acids accumulating in the coolant, and the treated regenerated coolant is returned to the system by way of line 59 from the purification apparatus (not shown).

Figure 2:
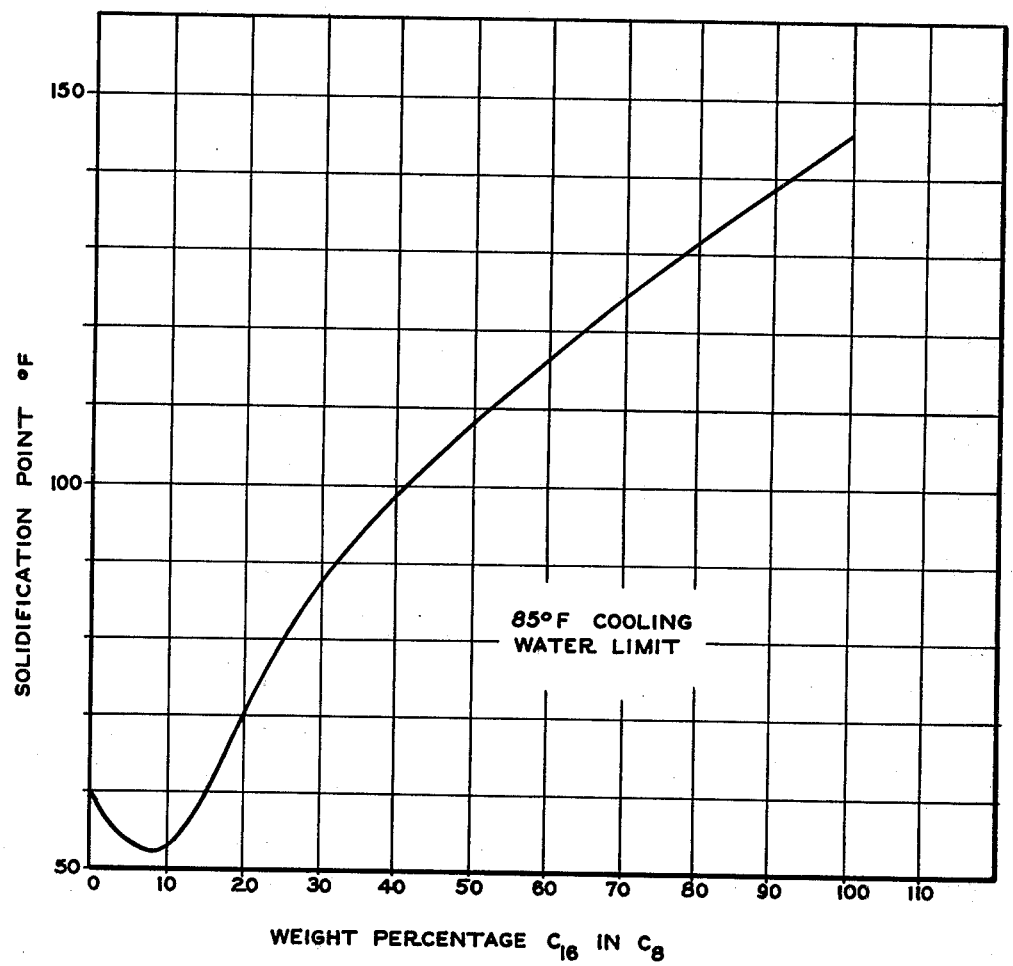

FIG. 2 shows a curve of the freezing point of palmitic acid dissolved in varying quantities in octanoic acid.

Referring to FIG. 2, the freezing point curve for a typical higher fatty acid, palmitic, dissolved in a lower fatty acid, octanoic acid, shows that at a practical temeprature as low as 85° F., a 30% solution of palmitic acid begins to crystallize. That is, using octanoic acid as a coolant permits an accumulation of 30% palmitic before purging is necessitated. The quantity of palmitic acid that octanoic acid as a solvent can hold before precipitation, as shown by the curve, will range upward from about 10% with the rising temperature. The use of unsaturated fatty acids such as oleic and linoleic would permit higher accumulations of palmitic.

In a typical operation using a fatty acid as the coolant, the amount of higher fatty acids condensed is limited by the cooling water temperature. For example, if the cooling water temperature is 85° F. and sufficient higher fatty acids have accumulated in the coolant to reduce the solidification point of the acids to 85° F., then blockage will occur in the cooler. Obviously, at this point coolant (containing condensed acids) is withdrawn and replaced with fresh coolant to reduce the higher acids content and to raise the solidification temperature. Using a cooling water temperature hotter than 85° F., say 100° F., will permit a greater accumulation of higher fatty acids in the coolant. For the octanoic coolant with palmitic acid accumulating (solidification points shown on FIG. 2) one might run to 25% by weight palmitic before replacing the coolant. This mixture has an 80° F. solidification point and will not cause blockage in a cooler using 85° F. water. A higher concentration of palmitic is permissable if a higher cooling water temperature, e.g. 100° F., is used. In this case about 40% by weight palmitic may be accumulated having a freeze point of 90° F. which is below the cooling water temperature of 100° F.

Replacement of coolant may be done continuously to just maintain the coolant mixture freeze point below that of the cooling water. Alternately the entire batch of coolant mixture may be replaced with a new batch of fresh coolant.

A significant feature of this invention is that a fatty acid coolant may be used that is miscible with the fatty acids entrained in the steam. It is often an advantage to use a lower fatty acid between 6 and 12 C-atoms, since such lower coolant fatty acids are easier to separate as coolant from higher fatty acids. However, where higher such as 15–18 combination of fatty acids are used as coolant they may not need to be separated from entrained fatty acids, a useful quanitity only being separated from the condensate for recycle as coolant. The recovered fatty acids and coolant can be returned to the processing plants for recovery of fatty acids and purification of coolant.

As a typical example, palmitic acid was considered as the coolant. However, other fatty acids, such as the unsaturated ones may also be used since they have a low freeze point. For example:

|  | Solid. Point |
|---|---|
| Oleic Acid | 37° F. |
| Linoleic Acid | 12° F. |

The selection of the specific acid to be used depends on the purification facilities available within the plant.

Consequently, in operation, the temperature will be controlled by surface exchange and the coolant will be supplied to the barometric condenser at a rate to condense all of the vapors, both the steam and the fatty acids and at a raised temperature above about 80° F. for optimum fluidity, and as high as 175° F. The condensed oil and water phases are separated by decantation and both of the separated phases are each treated separately to separate the higher fatty acids and water. A portion of the separated oil phase containing fatty acids is recycled for cooling, and the recovered water is returned to the plant for reuse. No water or cooling fluids that have been contacted with fatty acid is wasted to the sewers.

I claim:

1. The process of separating fatty acids from steam containing fatty acids entrained therein, comprising contacting the steam and fatty acids therein with a cooling medium comprising a fatty acid having between six and eighteen carbon atoms which is miscible with the fatty acids entrained in the steam passed directly to a barometric condenser to form a condensate of acid vapors, said cooling medium having a temperature above about 80° F., separating the resulting organic and water phases of the condensate by decantation, recycling a portion of the organic phase for use as the cooling medium, and processing the other separated liquid components for recovery of water and fatty acids.

2. The process of claim 1 wherein the cooling medium has a temperature in the range of about 80° F. to 175° F. and the condensate is maintained at a temperature in the range of 140° F. to 175° F.

3. The process of claim 1 wherein the cooling medium comprises a fatty acid between about six and twelve carbon atoms.

4. The process of claim 1 wherein the cooling medium comprises an unsaturated fatty acid having between fifteen and eighteen carbon atoms.

5. The process of claim 1 wherein the cooling medium contains about 10% and 40% by weight of higher fatty acids recovered from the steam.

6. The process of claim 1 wherein the cooling medium contains between 10% and 30% by weight of higher fatty acids recovered from the steam.

* * * * *